(12) United States Patent
Eidenschink (10) Patent No.: US 7,967,747 B2
(45) Date of Patent: Jun. 28, 2011

(54) FILTERING APPARATUS AND METHODS OF USE

(75) Inventor: Tracee E. J. Eidenschink, Wayzata, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 973 days.

(21) Appl. No.: 11/125,535

(22) Filed: May 10, 2005

(65) Prior Publication Data

US 2006/0259068 A1   Nov. 16, 2006

(51) Int. Cl.
*A61M 29/00* (2006.01)

(52) U.S. Cl. ........................................................ 600/200

(58) Field of Classification Search .................. 606/108, 606/151, 200, 191; 623/23.72, 1.1, 1.22; 600/585
See application file for complete search history.

(56) References Cited

U.S. PATENT DOCUMENTS

| | | |
|---|---|---|
| 3,868,956 A | 3/1975 | Alfidi et al. |
| 4,425,908 A | 1/1984 | Simon |
| 4,494,531 A | 1/1985 | Gianturco |
| 4,619,246 A | 10/1986 | Molgaard-Nielsen et al. |
| 4,643,184 A | 2/1987 | Mobin-Uddin |
| 4,781,177 A | 11/1988 | Lebigot |
| 4,793,348 A | 12/1988 | Palmaz |
| 4,832,055 A | 5/1989 | Palestrant |
| 4,950,224 A | 8/1990 | Gorsuch et al. |
| 4,957,501 A | 9/1990 | Lahille et al. |
| 4,969,891 A | 11/1990 | Gewertz |
| 4,990,156 A | 2/1991 | Lefebvre |
| 4,994,069 A | 2/1991 | Ritchart et al. |
| 4,998,539 A | 3/1991 | Delsanti |
| 5,108,420 A | 4/1992 | Marks |
| 5,133,733 A | 7/1992 | Rasmussen et al. |
| 5,265,622 A * | 11/1993 | Barbere ......................... 600/585 |
| 5,304,194 A | 4/1994 | Chee et al. |
| 5,329,942 A | 7/1994 | Gunther et al. |
| 5,350,398 A | 9/1994 | Pavenik et al. |
| 5,370,657 A | 12/1994 | Irie |
| 5,413,586 A | 5/1995 | Dibie et al. |
| 5,421,832 A | 6/1995 | Lefebvre |
| 5,527,338 A | 6/1996 | Purdy |
| 5,531,788 A | 7/1996 | Dibie et al. |
| 5,536,274 A | 7/1996 | Neuss |
| 5,601,595 A | 2/1997 | Smith |
| 5,626,605 A | 5/1997 | Irie et al. |
| 5,649,906 A | 7/1997 | Gory et al. |
| 5,695,518 A | 12/1997 | Laerum |

(Continued)

FOREIGN PATENT DOCUMENTS

EP          0 350 043 B1    1/1990

(Continued)

*Primary Examiner* — Todd E Manahan
*Assistant Examiner* — Jocelin C Tanner
(74) *Attorney, Agent, or Firm* — Seager, Tufte & Wickhem LLC (57) ABSTRACT

A filter apparatus for use in a body vessel lumen having a wall, which may include a first elongate member having a proximal end and a distal end, a second elongate member attached proximate a first end to the first elongate member and having a second end, and a plurality of connectors attached to the second elongate member at spaced-apart intervals of the second elongate member and slidably disposed on the first elongate member, the second elongate member movable between a first elongate configuration where the connectors are at a first average distance apart from each other and a second filtering configuration where the connectors are at a second average distance apart less than the first.

31 Claims, 9 Drawing Sheets

U.S. PATENT DOCUMENTS

| | | | |
|---|---|---|---|
| 5,700,258 A | 12/1997 | Mirigan et al. | |
| 5,720,764 A | 2/1998 | Naderlinger | |
| 5,733,294 A * | 3/1998 | Forber et al. | 606/151 |
| 5,797,953 A | 8/1998 | Tekulve | |
| 5,810,874 A | 9/1998 | Lefebvre | |
| 5,814,064 A | 9/1998 | Daniel et al. | |
| 5,836,968 A | 11/1998 | Simon et al. | |
| 5,836,969 A | 11/1998 | Kim et al. | |
| 5,846,261 A * | 12/1998 | Kotula et al. | 606/213 |
| 5,879,366 A | 3/1999 | Shaw et al. | |
| 5,893,869 A | 4/1999 | Barnhart et al. | |
| 5,928,260 A | 7/1999 | Chin et al. | |
| 5,935,139 A | 8/1999 | Bates | |
| 5,954,741 A | 9/1999 | Fox | |
| 5,984,947 A | 11/1999 | Smith | |
| 6,007,558 A | 12/1999 | Ravenscroft et al. | |
| 6,039,744 A | 3/2000 | Forber | |
| 6,059,825 A | 5/2000 | Hobbs et al. | |
| 6,080,178 A | 6/2000 | Meglin | |
| 6,126,673 A | 10/2000 | Kim et al. | |
| 6,146,396 A * | 11/2000 | Konya et al. | 606/159 |
| 6,251,122 B1 | 6/2001 | Tsukernik | |
| 6,267,776 B1 | 7/2001 | O'Connell | |
| 6,273,901 B1 | 8/2001 | Whitcher et al. | |
| 6,277,139 B1 * | 8/2001 | Levinson et al. | 606/200 |
| 6,402,736 B1 * | 6/2002 | Brown et al. | 604/523 |
| 6,482,222 B1 | 11/2002 | Bruckheimer et al. | |
| 6,558,404 B2 | 5/2003 | Tsukernik | |
| 6,582,447 B1 | 6/2003 | Patel et al. | |
| 6,773,448 B2 * | 8/2004 | Kusleika et al. | 606/200 |
| 6,783,538 B2 * | 8/2004 | McGuckin et al. | 606/200 |
| 6,793,665 B2 | 9/2004 | McGuckin, Jr. et al. | |
| 6,843,798 B2 | 1/2005 | Kusleika et al. | |
| 7,052,500 B2 * | 5/2006 | Bashiri et al. | 606/113 |
| 7,344,550 B2 * | 3/2008 | Carrison et al. | 606/200 |
| 2002/0193828 A1 | 12/2002 | Griffin et al. | |
| 2004/0193209 A1 | 9/2004 | Pavcnik et al. | |
| 2004/0199198 A1 * | 10/2004 | Beulke et al. | 606/200 |
| 2004/0199201 A1 * | 10/2004 | Kellett et al. | 606/200 |

FOREIGN PATENT DOCUMENTS

| | | |
|---|---|---|
| EP | 0 472 334 A1 | 2/1992 |
| WO | WO 95/09567 A1 | 4/1995 |
| WO | WO 98/02203 A1 | 1/1998 |
| WO | WO 00/18467 A1 | 4/2000 |

* cited by examiner

FILTERING APPARATUS AND METHODS OF USE

FIELD OF THE INVENTION

The present invention pertains to embolic protection. More particularly, the present invention pertains to embolic protection filters and methods of making the same.

BACKGROUND OF THE INVENTION

There are a number of situations in the practice of medicine when it becomes desirable for a physician to place a filter in the vascular system of a patient. One of the most common applications for vascular filters is the treatment of Deep Venous Thrombosis (DVT). Deep Venous Thrombosis patients experience clotting of blood in the large veins of the lower portions of the body. These patients are constantly at risk of a clot breaking free and traveling via the inferior vena cava to the heart and lungs. This process is known as pulmonary embolization. Pulmonary embolization can frequently be fatal, for example when a large blood clot interferes with the life-sustaining pumping action of the heart. If a blood clot passes through the heart it will be pumped into the lungs and may cause a blockage in the pulmonary arteries. A blockage of this type in the lungs will interfere with the oxygenation of the blood causing shock or death.

Pulmonary embolization may be successfully prevented by the appropriate placement of a thrombus filter in the vascular system of a patient's body. Placement of the filter may be accomplished by performing a laparotomy with the patient under general anesthesia. However, intravenous insertion is often the preferred method of placing a thrombus filter in a patient's vascular system.

Intravenous insertion of a thrombus filter is less invasive and it requires only a local anesthetic. In this procedure, the thrombus filter is collapsed within a delivery catheter. The delivery catheter is introduced into the patients vascular system at a point which is convenient to the physician. The delivery catheter is then fed further into the vascular system until it reaches a desirable location for filter placement. The thrombus filter is then released into the blood vessel from the delivery catheter.

In the treatment of Deep Venous Thrombosis, a thrombus filter is placed in the inferior vena cava of a patient. The inferior vena cava is a large vessel which returns blood to the heart from the lower part of the body. The inferior vena cava may be accessed through the patient's femoral or jugular vein.

Thrombus filters may be placed in other locations when treating conditions other than deep venous thrombosis. For example, if blood clots are expected to approach the heart and lungs from the upper portion of the body, a thrombus filter may be positioned in the superior vena cava. The superior vena cava is a large vessel which returns blood to the heart from the upper part of the body. The superior vena cava may also be accessed through the jugular vein or femoral vein.

Once placed inside a blood vessel, a thrombus filter acts to catch and hold blood clots. The flow of blood around the captured clots allows the body's lysing process to dissolve the clots.

Often, it is desirable to install thrombus filters through small lumens or through highly occluded lumens. It is therefore recognized in the art that it is desirable for a thrombus filter to be collapsible to a small diameter for installation through smaller or more occluded lumens.

SUMMARY OF THE INVENTION

One embodiment of the invention pertains to a filtering apparatus having a first elongate member, a second elongate member attached at a distal end to the first elongate member, and attached at a series of spaced apart connectors that are slideable disposed on the first elongate member. The filtering apparatus is movable between a first elongate configuration and a second filtering configuration. In the second filtering configuration, the connectors are near each other and the second elongate member forms into filtering loops. The filtering apparatus may include a push-lock, barbs, a distal tip or other components.

Another embodiment pertains to a filtering apparatus having a series of spaced-apart connectors, each proximate pair of connectors attached by a flexible elongate member, and each connector having another elongate member attached thereto and slideably disposed in the lumen of a proximal connector. The apparatus has a configuration where it has a first section of filtering loops and a second section of filtering or positioning legs.

The above summary of some embodiments is not intended to describe each disclosed embodiment or every implementation of the present invention. The figures and detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings in which.

DETAILED DESCRIPTION OF ILLUSTRATIVE EMBODIMENTS

The following description should be read with reference to the drawings, in which like elements in different drawings are numbered in like fashion. The drawings, which are not necessarily to scale, depict selected embodiments and are not intended to limit the scope of the invention. Although examples of construction, dimensions, and materials are illustrated for the various elements, those skilled in the art will recognize that many of the examples provided have suitable alternatives that may be utilized.

Figure 1:
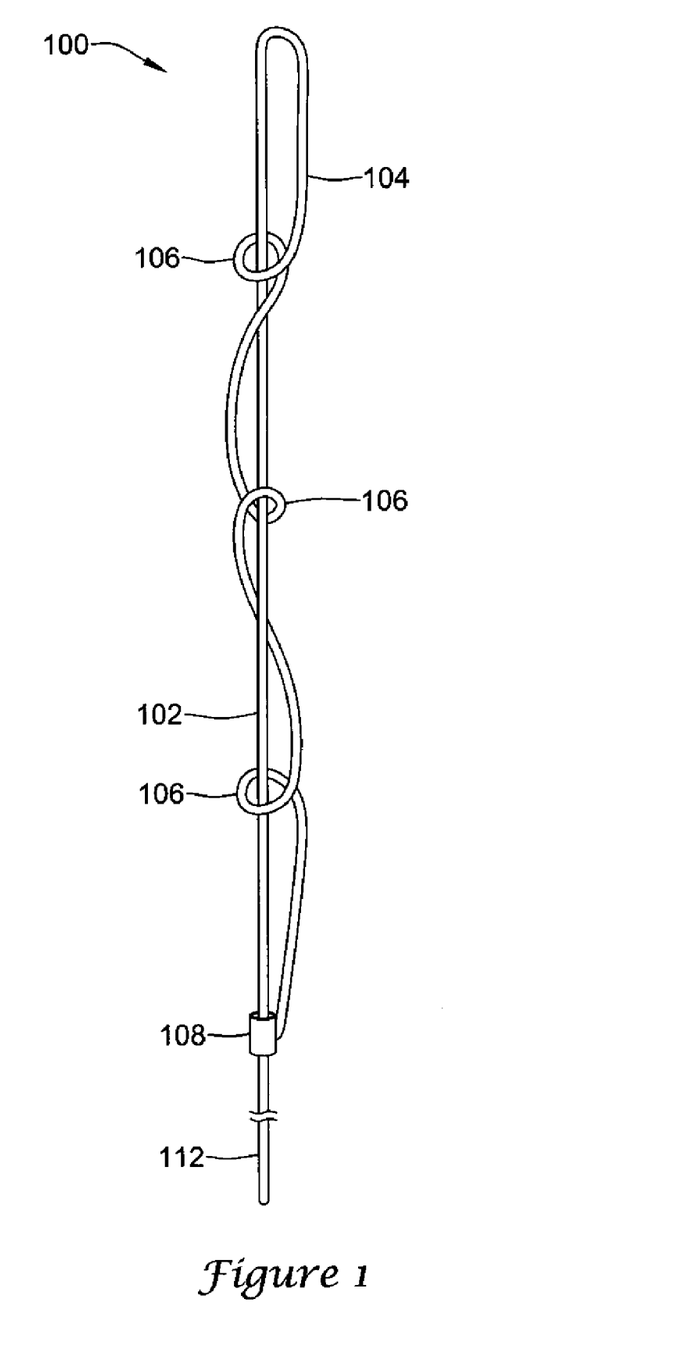
FIG. 1 is a side view of a filter apparatus 100 in a first configuration.
Figure 2:
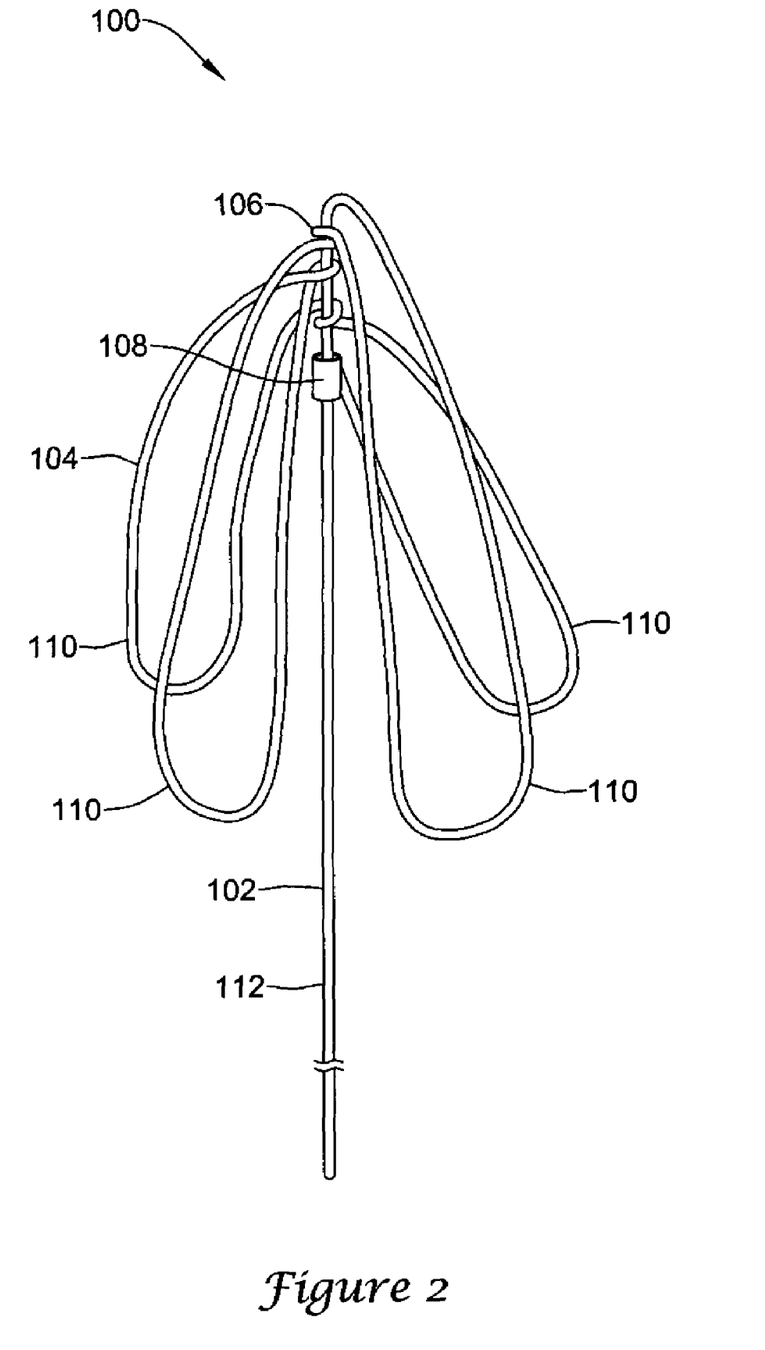
FIG. 2 is a perspective view of filtering apparatus 100 in a second configuration.

FIG. 1 is a side view of a filtering apparatus 100 in a first configuration. Filtering apparatus 100 includes a first elongate member 102 and a second elongate member 104. Elongate member 104 includes connectors 106 which are slideably disposed on elongate member 102. Connectors 106 are generally spaced apart at regular intervals as shown in FIG. 1. A push-lock 108 may be disposed on elongate member 104 near the proximal end. Connectors 106 and push-lock 108 may be advanced distally over elongate member 102 to produce a second configuration as shown in FIG. 2, which is suitable for capturing emboli. When connectors 106 are advanced distally, elongate member 104 may form filtering loops 110 configured in a cone-shaped filter having a proximal mouth and arms leading inward to a central apex. Elongate member 102 may have a detachment point 112 at which elongate member 102 may separate into two pieces.

Figure 3:
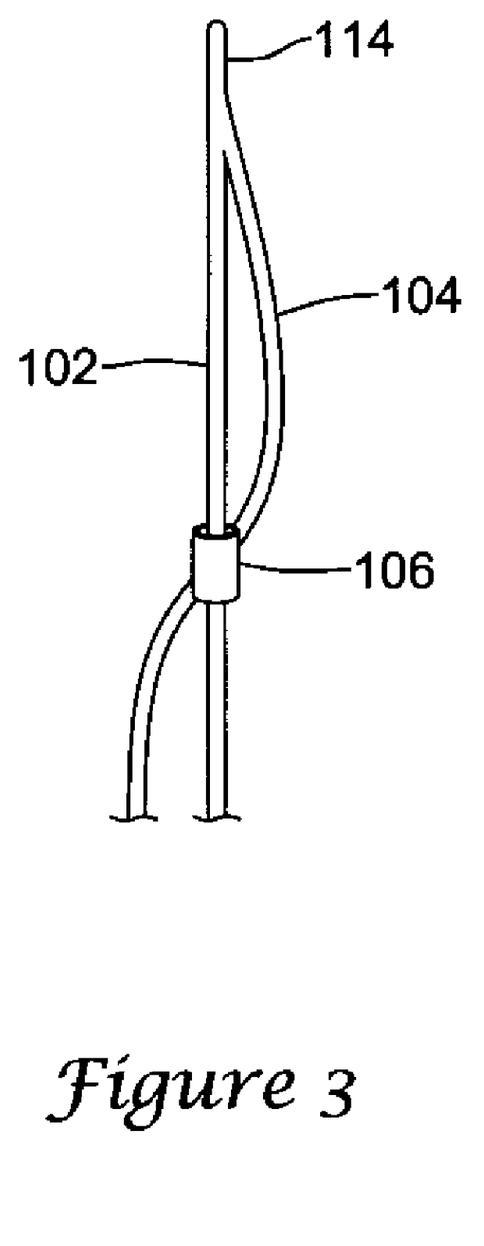
FIG. 3 is a side partial view of a filtering apparatus 200.

As can be seen in FIG. 1, connectors 106 are spaced along elongate member 102. The distance of the spacing between connectors 106 is shown as proximally equaled. The spacing, however, need not be equal. The average spacing between connectors 106 can be calculated by adding the distances between connectors 106 and dividing by the number of distances added. In FIG. 3, it can be seen that the average distance between connectors 106 is less than that shown in FIG. 1, as they have been slid towards one end of elongate member 102.

Connectors of filtering apparatus 100 are shown as loops formed from elongate member 104. The loops may be formed into connectors 106 by bending elongate member 104 and optionally securing the loop in place by welding, brazing, adhesive or other suitable technique. The connectors may also be other suitable devices. For examples, the connectors may be hollow cylinders or rings affixed to elongate member 104 by welding, or other suitable technique. The connectors may also be partially open, for example a c-shaped ring. Any devices suitable for slideably attaching elongate Member 104 to elongate member 102 may be suitable.

First elongate member 102 may be a substantially straight elongate wire. It may be made from any suitable materials, for example, stainless steel, nitinol, or a suitable polymer. The first elongate member may include a detaching point 112. In the embodiment of FIG. 1, the detaching point is proximal of the proximal end of the second elongate member when it is the first configuration. Other detachment points are contemplated. For example, a detachment point may be located just proximal the push-lock when the second elongate member is in the second filtering configuration, as shown in FIG. 2. The detachment point may be a threaded joint, a hook-and-eye joint, a ball-and-loop joint or other suitable joint. The first elongate member may have any suitable cross-sectional shape. For example, the cross-sectional shape may be circular (e.g., as shown in FIG. 1C), square (e.g., as shown for first elongate member 102' in FIG. 1D), hexagonal, or may have a slot (e.g., as shown for first elongate member 102" in FIG. 1E). The connectors may have a lumen shape suitable for tracking the shape of the first elongate member. For example, if the first elongate member has a square cross-section, the lumens of the connectors may also have a square cross-section of suitable size to slide along the first cross-section without rotating. This may aid in the positioning of the loops in the second configuration. In another alternative, the first elongate member may have a helical cross section so that the second elongate member rotates about the first elongate member as it forms the loops of the second filtering configuration.

Second elongate member 104 may be an elongate wire that has high flexibility. The second elongate member should be able to move from a substantially elongate configuration as shown in FIG. 1 to the second filtering configuration shown in FIG. 2. A stainless steel or nitinol material may be suitable. The second elongate member may have a circular cross section or may have an oblong cross section. The cross section of the second elongate member need not be uniform; it may change to facilitate bending at particular locations along the second elongate member. The cross-sectional area of the filter may vary depending on the flexibility desired. For example, if a greater amount of flexibility is desired, the second elongate member may be made from wire having a relatively small cross-sectional area. The second elongate member may be biased to be in the first configuration where it is substantially elongated. The second elongate member may have sufficient flexibility to be in a more elongate configuration, where the first and second elongate members are substantially parallel. For example, the filtering apparatus may be loaded in a catheter having a lumen only slightly larger than the connectors or the push-lock. The second elongate member may also be biased to the second configuration. That is, when released from the constraint of a catheter or other device, the second elongate member may assume the shape of the second configuration. Second elongate member is depicted as a single member, but may be a plurality of filaments, each filament being attached to one or more connectors. For example, one embodiment has a second elongate member made up of four filaments, each of the four filaments attached sequentially to each of the connectors.

Push-lock 108 is configured to permit distal movement and obstruct proximal movement. It may have, for example, proximal facing and inward spikes which bite into the shaft to prevent proximal movement but permit distal movement. In another embodiment, it has a first configuration that permits only distal movement and a second configuration that permits movement both proximally and distally. Alternatively, the push-lock may have a configuration which permits proximal and distal movement and a configuration in which it is locked to the first elongate member. The push lock may be actuated between the two alternatives by rotating a proximal portion of it or by another suitable method. The proximal portion may have teeth or detents which engage teeth or detents on the distal end of a catheter that slides over the first elongate member. The push-lock is shown as attached to the proximal end of second elongate member. In another alternative, a connector 106 is disposed at the proximal end of the second elongate member and the push-lock is located proximal of the connector and may or may not be attached to the second elongate member.

Figure 1A:
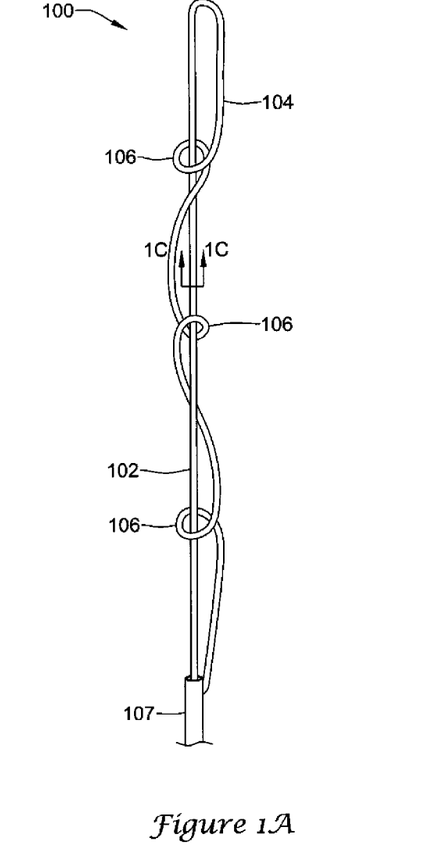
FIG. 1A is a side view of a filter apparatus 100 including a third elongate member 107.
Figure 1B:
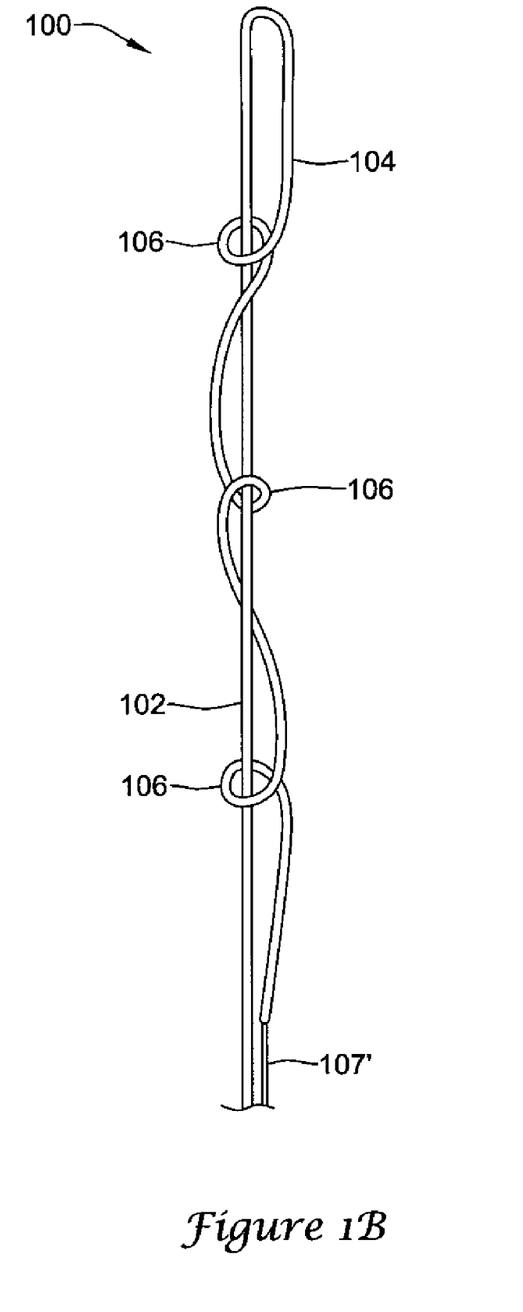
FIG. 1B is a side view of a filter apparatus 100 including a third elongate member 107'.
Figure 1C:
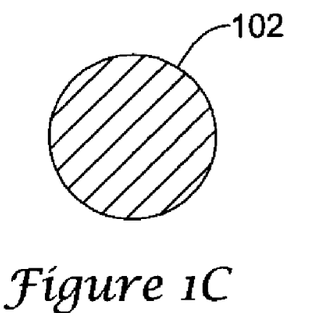
FIG. 1C is a cross-sectional view taken through line 3-3 in FIG. 1A.
Figure 1D:
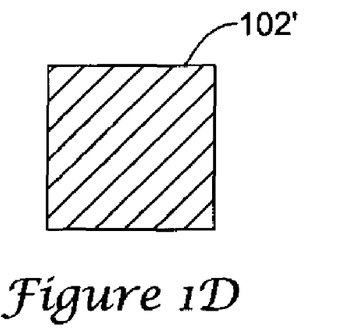
FIG. 1D is an alternative cross-sectional view taken through line 3-3 in FIG. 1A.
Figure 1E:
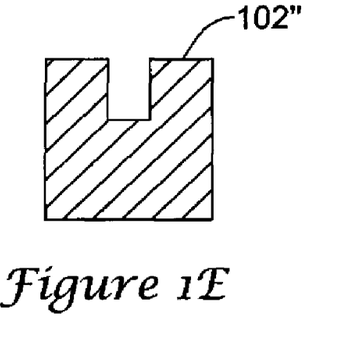
FIG. 1E is an alternative cross-sectional view taken through line 3-3 in FIG. 1A.

In an alternative embodiment lacking a push-lock, a third elongate member 107 extends proximally from the proximal end of the second elongate member as shown in FIG. 1A. This elongate member may be a catheter disposed over a proximal portion of the first elongate member (e.g., as shown in FIG. 1A) or may be a wire (e.g., as shown for third elongate member 107' in FIG. 1B). The third elongate member can be advanced proximally or distally relative to the first elongate member to move the second elongate member between the first and the second configurations. Of course, an embodiment having a third elongate member may include a push-lock. The third elongate member may be releasable from the second elongate member and may also control the push lock. In another alternative lacking a push-lock, the second elongate member is biased to the second configuration. When released from the constraint of a catheter or other device, the second elongate member assumes the second configuration.

Filtering loops 110 are configured to radiate outwardly from elongate member 102 in a radially uniform pattern to produce the filter. Four loops 110 are depicted, but any suitable number may be used. There may be, for example, three, five, six, seven, or eight loops. Loops 110 are shown as non-overlapping. In other embodiments, the filtering loops may overlap, or they may radiate out helically from the first elongate member. The loops are depicted as forming a conical-shaped filter, but the filter may be any suitable shape. For example, the filter may be bell-shaped. Each loop 110 is depicted as petal-shaped, but each loop may be any suitable shape. For example, the loop may be triangular. The angle of the loop may vary from being substantially normal to the axis of the first elongate member to any suitable angle. The angle of the loop may vary along the length of the loop. For example, the filtering loops may extend out at a first angle to produce a conical filter portion and then extend at a second angle that lies along the wall of the vessel lumen. The filter is shown as having a proximally facing mouth, but the loops may be configured to produce a distally facing mouth. The filtering loops may also include outward protrusions designed to retain the position of the filter against the vessel wall. For example, the filtering loops may have ends shaped like "W"s with the central portion of the "W" extending radially outward from the side branches of the "W".

The filtering loops may also include an anchoring member such as a needle, hook, barb, or prong that can be used to further secure the filter to the wall of the vessel. The anchoring members may be configured to not scrape the wall of the vessel during deployment. For example, the sharp end of the barb may be pointed away from the direction of movement during deployment of the second elongate member. In another alternative, the barb is retained in a non-piercing state during deployment by a compound which will dissolve in the fluid stream to free the barb.

The filtering apparatus may include a therapeutic agent. For example, it may be desirable to coat the second elongate member with an agent that enhances clotting or lysing, or an agent which reduces neointimal hyperplasia, or another suitable compound.

The filtering apparatus may also include a distal tip 114. Filtering apparatus 100 is depicted as having a rounded tip where the first elongate member and the second elongate member are connected. An alternate construction is shown in FIG. 3. In the embodiment shown in FIG. 3, elongate member 102 and elongate member 104 are attached at an acute angle to each other. Of course, any suitable angle may be used. Extending distally from the joint is a distal tip. The tip may have an atraumatic, or floppy end, or other suitable configuration. Radiopaque materials such as gold, tantalum, or platinum may be used as desired with various components of the filtering apparatus to provide desired radiopaque visualization.

Figure 4:
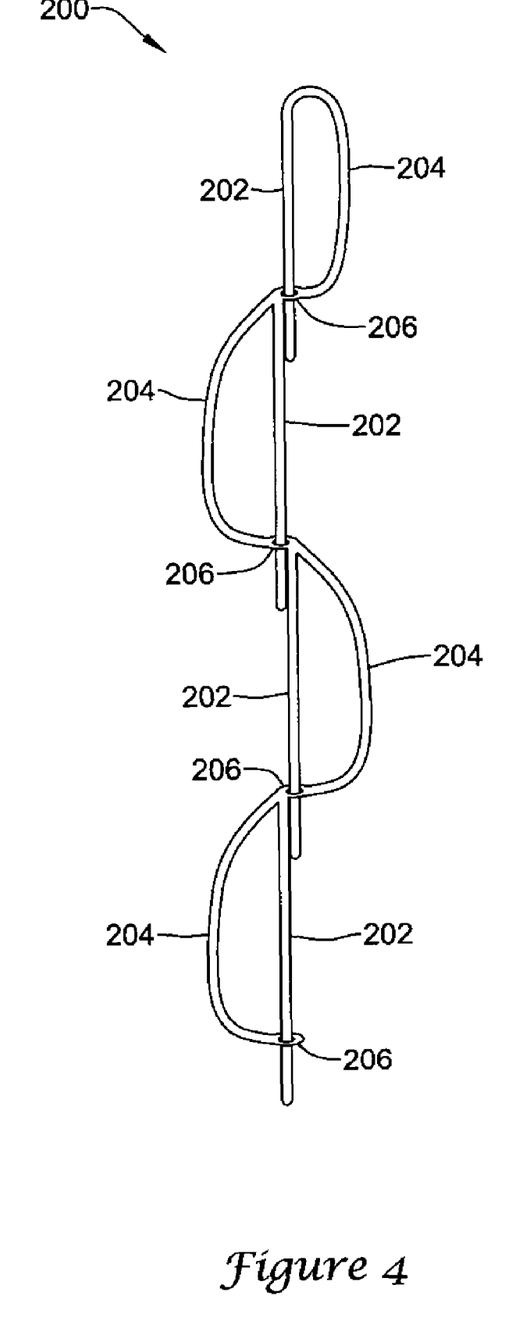
FIG. 4 is a side view of a filtering apparatus 300 in a first configuration.

A side view of a filtering apparatus 200 in a first configuration is depicted in FIG. 4. Filtering apparatus 200 includes a plurality of connectors 206, which are spaced apart in the first configuration. An elongate member 202 may be attached to each connector and be slideably disposed in a proximal connector lumen. In FIG. 4, each elongate member 202 is disposed in the nearest proximal connector lumen. Elongate members 204 are connected between each proximate pair of connectors. An elongate member 204 extends distally from the distalmost connector and is attached to an elongate member 202 which is slidingly disposed in the distalmost connector.

Figure 5:
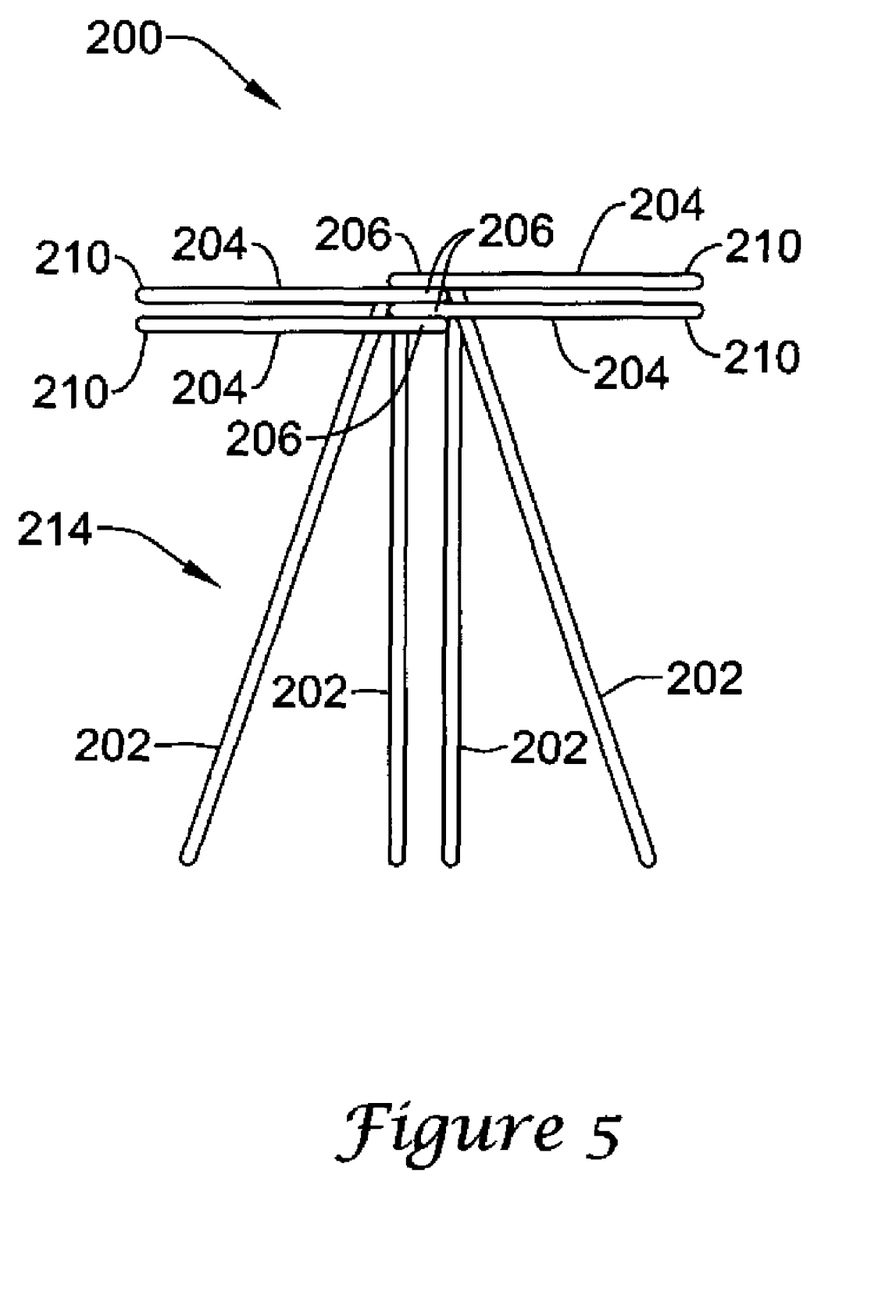
FIG. 5 is a side view of filtering apparatus 300 in a second configuration.
Figure 6:
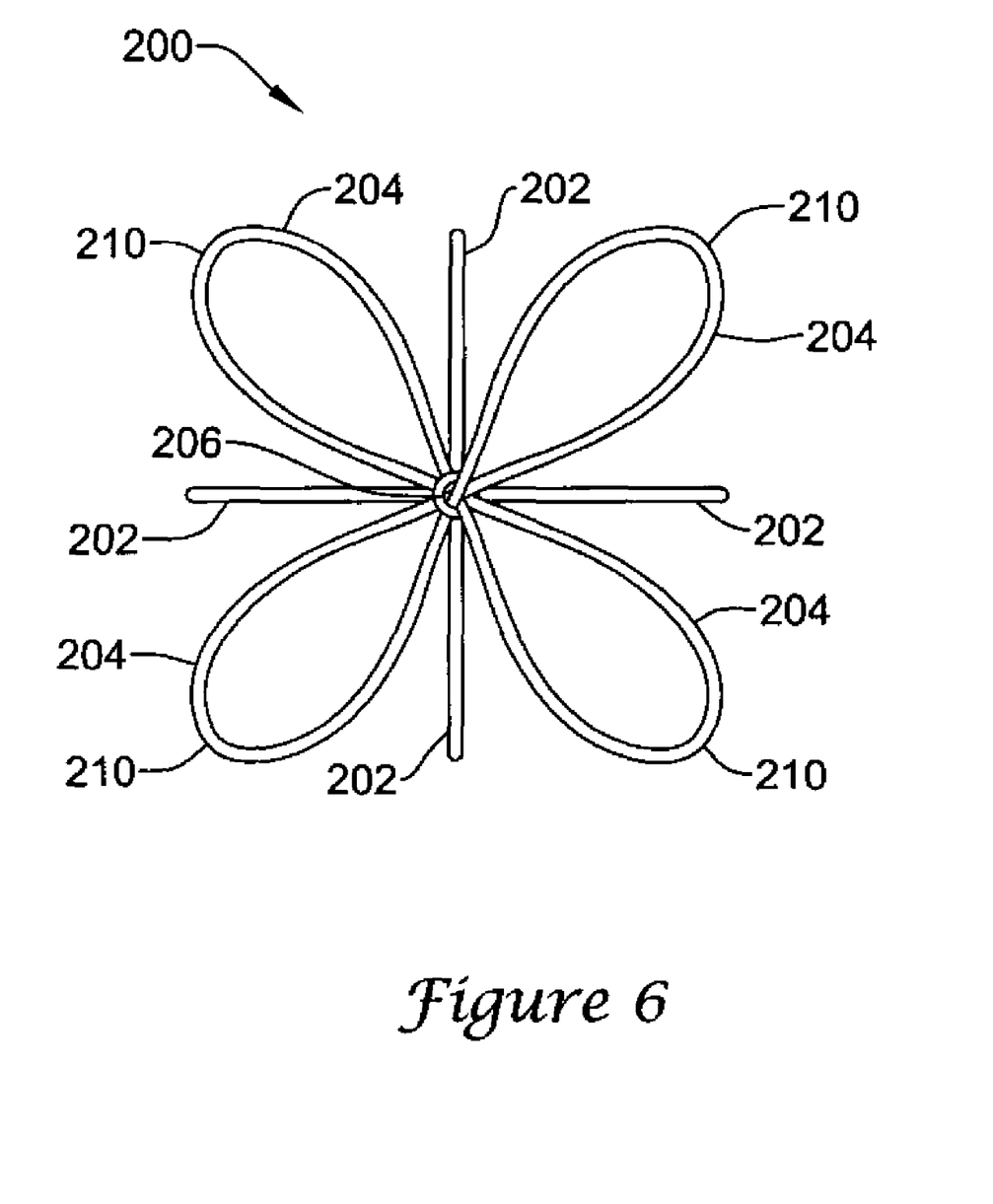
FIG. 6 is a top view of filtering apparatus 300 in the second configuration.

Filtering apparatus 200 is movable between the first configuration, depicted in FIG. 4, and a second configuration, a side view of which is depicted in FIG. 5 and a top view of which is depicted in FIG. 6. Filtering apparatus 200 may be biased towards the second configuration. Thus when released from a constraint such as a catheter, elongate members 204 form filtering loops 210 and move connectors 206 together. Elongate members 202 are advanced proximally through connectors 206 and extend radially outward and in a proximal direction to form a cone 214, which may be suitable for filtering or for positioning. The second configuration filtering loops and cone may have approximately the same radial extent, so that both the loops and the cone touch the wall of the vessel lumen to help position the filter. It is contemplated that filtering apparatus 200 may be modified in many of the ways described above with respect to filtering apparatus 100. For example, the number of loops may be modified. As another example, the filtering loops may form a cone or bell shaped, rather than be substantially flat as pictured. In another example modification, the distal tip depicted in FIG. 3 may be used. Filtering apparatus 200 may also be modified in other ways as well. For example, an elongate member 202 may extend proximally from the proximalmost connector 206. In another example, connectors 206 may twist helically when in the second configuration, and may include anchoring members such as needles or barbs. In use, filtering apparatus 200 may be loaded in a catheter, the catheter may be advanced to a desired filtering location, and the filtering apparatus may be advanced from the catheter to form the second configuration.

A filtering apparatus 100 may be loaded in a catheter, and the catheter may be advanced to a desired filtering location. If the catheter is too large to fit through an occlusion, the filtering apparatus may be advanced distally from the catheter through the occlusion. The filtering apparatus may then be moved into the second configuration by advancing the push-lock distally over the first elongate member or by retracting the first elongate member distally. The proximal portion of the first elongate member may be removed at the attachment point if desired. The filtering apparatus may be removed by releasing the push-lock and moving the filtering apparatus to the first configuration. The filtering apparatus may then be retracted inside a catheter and removed from the body lumen. Of course, other methods of operation are suitable for use with embodiments of apparatus 100.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A filter apparatus for use in a body vessel lumen having a wall, comprising:
   a first elongate member having a proximal end and a distal end; and
   a second elongate member having a first end and a second end, the first end attached to the first elongate member at the distal end;
   wherein the second elongate member is a wire including a plurality of closed connectors each disposed at spaced-apart intervals of the second elongate member and each slidably disposed on the first elongate member;
   wherein each of the plurality of closed connectors are formed as loops of the wire, each loop having a first portion, a second portion, and a joining portion connecting the first portion to the second portion, wherein the first portion is secured to the second portion opposite the joining portion to enclose the first elongate member therein;

wherein the plurality of closed connectors includes a first connector, a third connector, and a the second connector disposed between the first connector and the third connector;

wherein the second elongate member is movable between a first elongate configuration where the connectors are at a first average distance apart from each other and a second filtering configuration where the connectors are disposed proximate the distal end of the first elongate member at a second average distance apart less than the first;

wherein the second elongate member forms a first loop between the first connector and the second connector when the second elongate member is in the second filtering configuration;

wherein the second elongate member forms a second loop between the second connector and the third connector when the second elongate member is in the second filtering configuration;

wherein the first loop and the second loop each have a first section, a second section, and a joining section connecting the first section to the second section;

wherein the first sections and the second sections of the first and second loops are configured to radiate outwardly and proximally from proximate the distal end of the first elongate member to form a generally cone-shaped filter;

wherein the joining sections of the first and second loops are disposed proximal of the first and second sections of their respective loops;

wherein the first loop radiates outwardly from the first elongate member at a first polar angle when viewed along a longitudinal axis of the first elongate member from the distal end, and the second loop radiates outwardly from the first elongate member at a second polar angle when viewed along the longitudinal axis from the distal end, the first polar angle being different from the second polar angle.

2. The apparatus of claim 1, wherein the connectors are annular.

3. The apparatus of claim 1, wherein the first and second portions are secured by a process selected from the group of soldering, welding, and epoxy.

4. The apparatus of claim 1, wherein the first elongate member is detachable from the second elongate member.

5. The apparatus of claim 1, wherein the first elongate member has a proximal section detachable from a distal section at a detachment point.

6. The apparatus of claim 5, wherein the detachment point is near and proximal the second elongate member when the second elongate member is in the second filtering configuration.

7. The apparatus of claim 5, wherein the detachment point is proximal the second elongate member when the second elongate member is in the first elongate configuration.

8. The apparatus of claim 1, further comprising a locking mechanism attached to the second elongate member in the direction of the second end from the plurality of connectors and engaged with the first elongate member.

9. The apparatus of claim 8, wherein the locking mechanism has a first state where it is movable in a first direction along the first elongate member and where it resists movement in a second direction opposite the first direction.

10. The apparatus of claim 9, wherein the locking mechanism has a second state where it is movable in the second direction.

11. The apparatus of claim 1, further comprising a third elongate member attached to the second end of the second elongate member and extending substantially parallel with the first elongate member.

12. The apparatus of claim 11, wherein the third elongate member is detachable from the second elongate member.

13. The apparatus of claim 11, wherein the third elongate member is a wire.

14. The apparatus of claim 1, further comprising a third elongate member attached to the second end of the second elongate member and, wherein the third elongate member is a catheter having a lumen therethrough.

15. The apparatus of claim 14, wherein the first elongate member is at least partially disposed in the lumen of the third elongate member.

16. The apparatus of claim 1, wherein the second elongate member is biased to be in the first elongate configuration.

17. The apparatus of claim 1, wherein the second elongate member is biased to be in a third biased configuration where the connectors are at a third average distance apart, the third average distance being between the first average distance and the second average distance.

18. The apparatus of claim 1, wherein the second elongate member is biased to be in the second filtering configuration.

19. The apparatus of claim 1, wherein the first elongate member has a non-circular cross section, and wherein the plurality of connectors are configured to slide longitudinally on the first elongate member without rotation.

20. The apparatus of claim 19, wherein the cross section is square.

21. The apparatus of claim 19, wherein the cross section includes a slot.

22. The apparatus of claim 1, further comprising a distal tip near the distal end of the first elongate member.

23. The apparatus of claim 1, wherein the second elongate member comprises an highly elastic material.

24. The apparatus of claim 23, wherein the highly elastic material is a stainless steel.

25. The apparatus of claim 23, wherein the highly elastic material is a superelastic material.

26. The apparatus of claim 25, wherein the superelastic material is a nickel-titanium alloy.

27. A method of filtering emboli in a body vessel lumen, comprising the steps of:

obtaining an apparatus having a first elongate member having a proximal end and a distal end, a second elongate member having a proximal end and a distal end attached to the distal end of the first elongate member, a plurality of closed connectors including a first connector, a second connector, and a third connector attached to the second elongate member at spaced-apart intervals and slidably disposed on the first elongate member;

inserting the apparatus in a body vessel lumen; and advancing the connectors distally relative to the first elongate member to form the second elongate member into a series of loops including a first loop between the first connector and the second connector and a second loop between the second connector and the third connector radiating outward from the first elongate member;

wherein the series of loops forms a conical filter having proximally-facing mouth and a distally-oriented central apex, the series of loops each extending outwardly and proximally from the central apex at a different polar angle when viewed along a longitudinal axis of the first elongate member from the distal end, and the first connector, second connector, and third connector being disposed proximate the central apex.

28. The method of claim 27, further comprising the steps of loading the apparatus in the lumen of a catheter, and advancing the apparatus from the distal end of the catheter.

29. The method of claim 27, wherein the step of advancing the connectors distally includes the step of moving the connectors closer together.

30. The method of claim 27, further comprising the step of detaching a proximal portion of the first elongate member.

31. The method of claim 27, wherein the apparatus further comprises a push-lock disposed on the first elongate member proximal the connectors, the push-lock having a configuration which prevents proximal movement, and having a configuration wherein the push-lock is slidable distally.

* * * * *